(12) United States Patent
Tepe et al.

(10) Patent No.: US 8,252,942 B2
(45) Date of Patent: *Aug. 28, 2012

(54) SUBSTITUTED IMIDAZOLINE COMPOUNDS

(75) Inventors: Jetze Tepe, East Lansing, MI (US);
James Hamby, Ann Arbor, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 91 days.

This patent is subject to a terminal disclaimer.

(21) Appl. No.: 12/247,524

(22) Filed: Oct. 8, 2008

(65) Prior Publication Data

US 2009/0156830 A1    Jun. 18, 2009

(51) Int. Cl.
*C07D 233/22* (2006.01)

(52) U.S. Cl. .................................................. 548/334.5

(58) Field of Classification Search ........................ None
See application file for complete search history.

(56) References Cited

U.S. PATENT DOCUMENTS

| 2003/0232870 A1* | 12/2003 | Tepe et al. | 514/401 |
| 2005/0020586 A1* | 1/2005 | Tepe | 514/227.5 |
| 2008/0114015 A1* | 5/2008 | Tepe | 514/283 |

OTHER PUBLICATIONS

Berge et al. J. Pharm. Sci., 1977, 66 (1), 1-19.*
Patani et al. Chem Rev., 1996, 96, 3147-76.*
Peddibhotla et al., Org. Lett., vol. 4, No. 20, 2002.*
Sharma et al. (J. Am. Chem. Soc., (2006), 128, pp. 9137-9143).*

* cited by examiner

*Primary Examiner* — Joseph K. McKane
*Assistant Examiner* — Alicia L Otton
(74) *Attorney, Agent, or Firm* — Medlen + Carroll, LLP

(57) ABSTRACT

The invention relates to compositions comprising substituted imidazoline compounds including prodrugs, and salts thereof. In some embodiments, the invention relates to the use of these compositions as therapeutic agents, preferably for the treatment of arthritis or cancer. In further embodiments, The invention relates to the pharmaceutical compositions with effective amounts of substituted imidazoline compounds disclosed herein that function as agonist or antagonists of the genetic expression or interactions with transcription factor NF-κB.

1 Claim, 11 Drawing Sheets

| Structure (all racemic) Carboxylic Acid | Name | EC$_{50}$ Luciferase | IC$_{50}$ Human blood |
|---|---|---|---|
| Ph, Ph, CO$_2$Me, N-N, Ph-Bn, Ph | TCH-019 | 4.6 (±1.3) μM | 1.2 (±1.5) μM |
| Ph, Ph, CO$_2$Et, N-N, Ph-Bn, Ph | TCH-013 | 2.7 (±1.0) μM | 3.2 (±1.2) μM |
| Ph, Ph, CO$_2$Bn, N-N, Ph-Bn, Ph | TCH-020 | 1.8 (±1.3) μM | Not yet tested |
| Ph, Ph, CONH$_2$, N-N, Ph-Bn, Ph | TCH-015 | 10.0 μM | 10.4 (±1.2) μM |

FIG 2

| | TCH-number | R-group |
|---|---|---|
| (imidazoline structure with Ph, Ph, Ph, Ph, R₄) | | $R_4 =$ |
| 1 | TCH-019 | $CO_2Me$ |
| 2 | TCH-013 | $CO_2Et$ |
| 3 | TCH-020 | $CO_2Bn$ |
| 4 | TCH-015 | $CONH_2$ |
| 5 | TCH-024 | $CH_2OH$ |
| (imidazoline structure with R₅, Ph, Ph, CO₂Et, Ph) | | $R_5 =$ |
| 6 | TCH-023 | H |
| 7 | TCH-022 | (benzoyl group) |
| 8 | TCH-029 | (4-bromobenzyl group) |
| (imidazoline structure with Ph, Ph, R₁, CO₂Et, Ph) | | $R_1 =$ |
| 9 | TCH-028 | (4-bromophenyl group) |

FIG 3

| | | $R_4$ |
|---|---|---|
| 10 | TCH-021 | $CO_2Et$ |
| 11 | RM-2-055 | $CH_2OH$ |
| 12 | RM-2-071 | $CH_2N_3$ |
| 13 | TCH-025 |  |
| 14 | TCH-027 |  |
| 15 | TCH-026 |  |
| | | $R_5$ = |
| 16 | RM-2-037 | H |
| 17 | RM-2-143 |  |

| Compound | HeLa NF-κB-luc Log EC$_{50}$ | HeLa NF κB-luc Std. Err log EC$_{50}$ | HeLa NF-κB-luc EC$_{50}$ | Whole Blood TNF-α Log IC$_{50}$ | Whole Blood TNF-α Std. Error Log IC$_{50}$ | Whole Blood TNF-α IC$_{50}$ | Whole Blood IL-6 Log IC$_{50}$ | Whole Blood IL-6 Std. Err Log IC$_{50}$ | Whole Blood IL-6 IC$_{50}$ |
|---|---|---|---|---|---|---|---|---|---|
| 1 | 0.40 | 0.04 | 2.5 μM | 0.07 | 0.04 | 1.2 μM | -0.10 | 0.05 | 0.8 μM |
| 1b | 0.21 | 0.10 | 1.6 μM | -0.18 | 0.07 | 0.6 μM | -0.64 | 0.09 | 0.2 μM |
| 1a | 0.47 | 0.11 | 2.9 μM | -0.13 | 0.05 | 0.7 μM | -0.23 | 0.05 | 0.6 μM |
| 3 | 1.04 | 0.03 | 11.0 μM | - | - | - | 0.38 | 0.16 | 2.4 μM |
| 4 | 0.66 | 0.07 | 4.6 μM | - | - | - | 0.39 | 0.03 | 2.5 μM |
| 5 | 1.44 | 1.27 | >20 μM | - | - | - | - | - | - |
| 6 | 0.87 | 0.01 | 7.5 μM | 0.45 | 0.08 | 2.8 μM | 0.48 | 0.11 | 3.0 μM |
| 7 | 0.54 | 0.11 | 3.5 μM | 0.51 | 0.13 | 3.2 μM | 0.77 | 0.33 | 5.9 μM |
| 8 | 1.55 | 0.06 | ~20 μM | 1.67 | 0.27 | >20 μM | 1.67 | 0.55 | >20 μM |
| 9 | -2.1e+7 | 1.8e+014 | >20 μM | 1.07 | 0.15 | 11.9 μM | 1.29 | 12432 | ~20 μM |

FIG 6

| Compound | R² | HeLa NF kB-luc Log EC₅₀ | HeLa NF kB-luc Std. Err. log EC₅₀ | HeLa NF kB-luc EC₅₀ | Whole Blood IL-6 Log IC₅₀ | Whole Blood IL-6 Std. Err. Log IC₅₀ | Whole Blood IL-6 IC₅₀ |
|---|---|---|---|---|---|---|---|
| 10 | Ph | 0.87 | 0.01 | 7.5 µM | 0.48 | 0.11 | 3.0 µM |
| 11 | Me | -9.6x10⁶ | 2.4x10¹³ | >20 µM | 0.47 | 0.05 | 3.0 µM |
| 12 | ⁱPr | 1.37 | 0.09 | ~20 µM | 0.85 | 0.03 | 7.1 µM |
| 13 | methyl-indol | 1.11 | 0.05 | 13.0 µM | 1.21 | 0.20 | 16.1 µM |
| 14 | Bn | 0.72 | 0.04 | 5.3 µM | 0.61 | 0.07 | 4.1 µM |

FIG 7

| Compound | R⁴ | HeLa NF κB-luc Log EC₅₀ | HeLa NF κB-luc Std. Error log EC₅₀ | HeLa NF κB-luc EC₅₀ | Whole Blood IL-6 Log IC₅₀ | Whole Blood IL-6 Std. Error Log IC₅₀ | Whole Blood IL-6 IC₅₀ |
|---|---|---|---|---|---|---|---|
| 23 | H | 2.06 | 1.03 | >20 μM | 1.54 | 0.14 | >20 μM |
| 24 | Ac | 2.22 | 1.82 | >20 μM | - | - | >20 μM |
| 25 | Bz | 1.40 | 0.04 | ~20 μM | 0.82 | 0.06 | 6.6 μM |
| 26 | Tos | 1.56 | 0.46 | ~20 μM | 0.82 | 0.14 | 6.6 μM |
| 27 | 4-Bn-OMe | 0.69 | 0.06 | 4.6 μM | .014 | 0.03 | 1.4 μM |
| 28 | 4-Bn-Me | 0.23 | 0.10 | 1.7 μM | 0.66 | 0.05 | 4.6 μM |
| 29 | 4-Ph-Br | 0.44 | 0.05 | 2.7 μM | -0.30 | 0.02 | 0.5 μM |
| 30 | 4-Ph-Cl | 0.62 | 0.05 | 4.2 μM | 0.20 | 0.12 | 1.6 μM |
| 31 | 4-Ph-F | 0.71 | 0.03 | 5.2 μM | 0.08 | 0.02 | 1.2 μM |
| 32 | 4-Ph-CF₃ | 0.82 | 0.05 | 5.5 μM | 0.17 | 0.03 | 1.5 μM |
| 33 | 2-Furan | 0.74 | 0.05 | 4.2 μM | 0.11 | 0.02 | 1.3 μM |

FIG 9

SUBSTITUTED IMIDAZOLINE COMPOUNDS

FIELD OF INVENTION

The invention relates to compositions comprising substituted imidazoline compounds including prodrugs, enantiomers and salts thereof. In some embodiments, the invention relates to the use of these compositions as therapeutic agents, preferably for the treatment of arthritis or cancer. In further embodiments, The invention relates to the pharmaceutical compositions with effective amounts of substituted imidazoline compounds disclosed herein that function as agonist or antagonists of the genetic expression or interactions with transcription factor NF-κB.

BACKGROUND

The NF-kappaB/Rel signaling system is a paradigm for gene activation in response to inflammatory and menacing stimuli. A growing body of evidence provides a significant role of NF-kappaB for the onset of autoimmune diseases and different types of cancer. NF-kappaB is a drug target for the adjuvant therapy of these diseases. U.S. Pat. No. 6,878,735 discloses multi-substituted imidazolines as inhibitors or NF-κB. However, there remains a need for improved NF-κB inhibitors that have optimized therapeutic properties such as improved efficacy and reduced adverse drug reactions.

SUMMARY OF INVENTION

The invention relates to compositions comprising substituted imidazoline compounds including prodrugs, and salts thereof. In some embodiments, the invention relates to the use of these compositions as therapeutic agents, preferably for the treatment of arthritis or cancer. In further embodiments, The invention relates to the pharmaceutical compositions with effective amounts of substituted imidazoline compounds disclosed herein that function as agonist or antagonists of the genetic expression or interactions with transcription factor NF-κB.

In some embodiments, the invention relates to compound selected from the group consisting of:

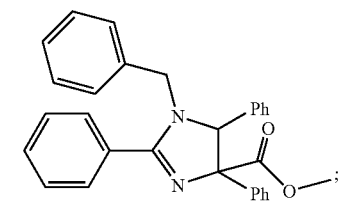

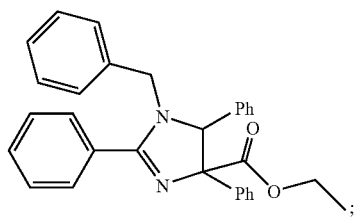

-continued

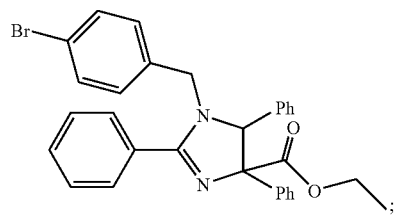

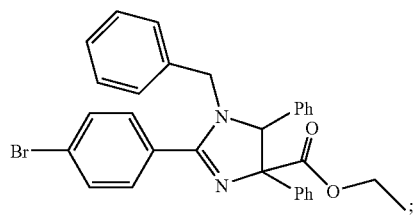

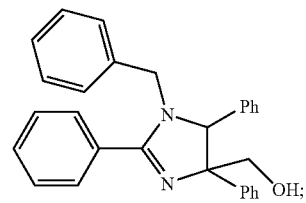

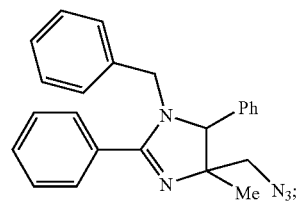

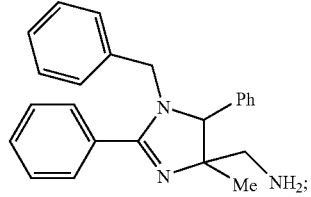

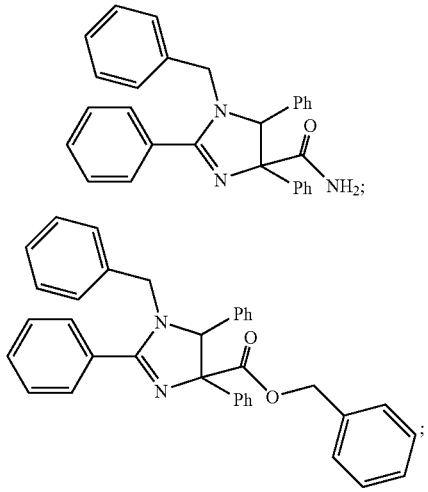

-continued

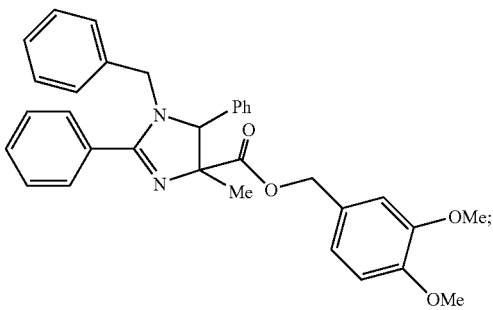

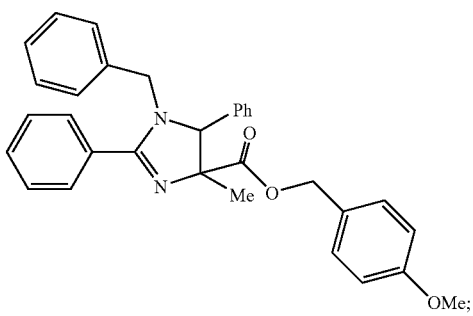

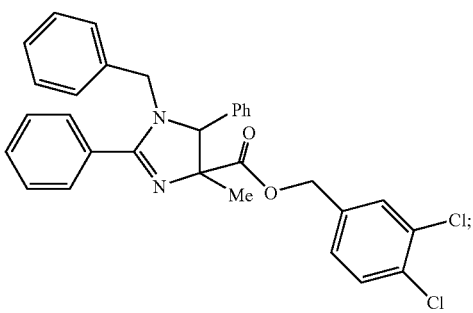

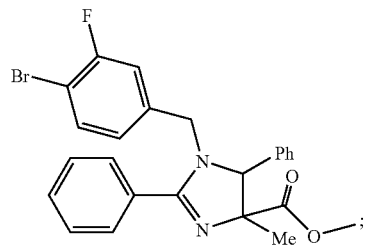

or salts thereof.

In some embodiments, the invention relates to a substituted or unsubstituted compound having the following formula:

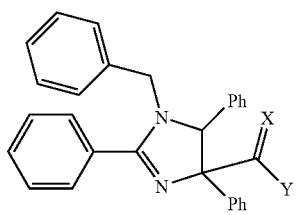

or salts thereof wherein: X is =O, or two hydrogen atoms each bound by single bonds to the adjacent carbon atom; and Y is amino, substituted amino, alkylamino, substituted alkyl amino, alkyloxy, substituted alkyloxy, arylalkyloxy, or substituted arylalkyloxy. In further embodiments, said compound is substituted with a halogen or alkyloxy. In further embodiments, said alkyloxy is ethoxy or methoxy. In further embodiments, said arylalkyloxy is a phenylmethyloxy. In further embodiments, said substituted arylalkyloxy is substituted with a halogen or alkyloxy. In further embodiments, said salt is a pharmaceutically acceptable salt.

In some embodiments, the invention relates to a substituted or unsubstituted compound having the following formula:

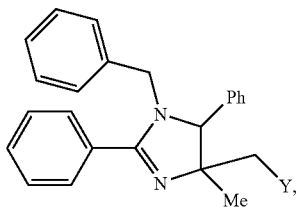

or salts thereof; wherein Y is azido, amino, substituted amino, alkylamino, or substituted alkylamino. In further embodiments, said salt is a hydrochloride salt.

In some embodiments, the invention relates to a compound comprising a substituted or unsubstituted compound having the following formula:

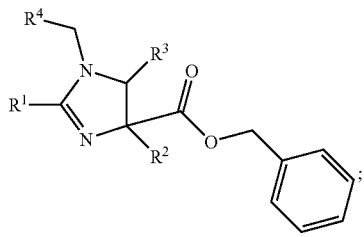

or salts thereof; wherein $R^1$, $R^2$, $R^3$, and $R^4$ are the same or differently and independently alkyl, substituted alkyl, aryl, or substituted aryl. In further embodiments, said compound is substituted with one or more a halogen or alkyloxy. In further embodiments, said aryl is phenyl. In further embodiments, said salt is a hydrochloride salt.

In some embodiments, the invention relates to a salt of a compound having the following formula:

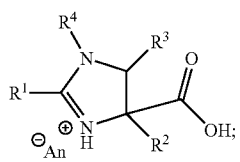

wherein $R^1$, $R^2$, $R^3$, and $R^4$ are the same or differently and independently at each occurrence alkyl, substituted alkyl, aryl, or substituted aryl; and An is an anion. In further embodiments, said anion is a chlorine anion.

In some embodiments, the invention relates to a salt of a compound having the following formula:

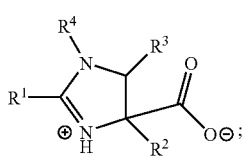

wherein $R^1$, $R^2$, $R^3$, and $R^4$ are the same or differently and independently at each occurrence alkyl, substituted alkyl, aryl, or substituted aryl.

In some embodiments, the invention relates to a salt of a compound having the following formula:

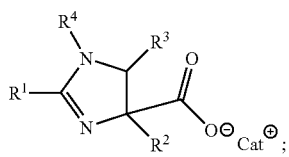

wherein $R^1$, $R^2$, $R^3$, and $R^4$ are the same or differently and independently at each occurrence alkyl, substituted alkyl, aryl, or substituted aryl, and $Cat^+$ is a cation.

In some embodiments, ester derivatives are contemplated such as the following:

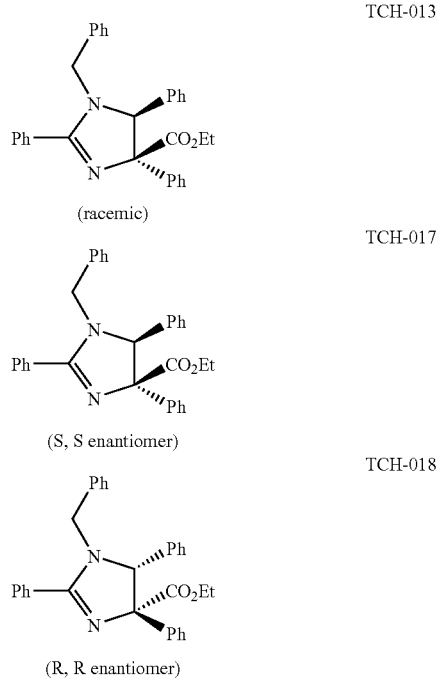

While not intending to limit the invention in any manner, it appears that the RR enantiomer of TCH-013 is slightly more potent than the SS enantiomer.

In some embodiments, the invention relates to a composition, preferably a pharmaceutical composition comprising substituted imidazoline compounds disclosed herein and a pharmaceutically acceptable excipient.

In some embodiments, the invention relates to a method of preventing, treating, or managing an inflammatory disease, preferably rheumatoid arthritis, comprising providing a subject diagnosed with, at risk for, or exhibiting symptoms of said disease and a composition comprising a substituted imidazoline compound disclosed herein, and administering said composition to said subject.

In some embodiments, the invention relates to a method of preventing, treating, or managing cancer comprising providing a subject diagnosed with, at risk for, or exhibiting symptoms of cancer and a composition comprising a substituted imidazoline compound disclosed herein, and administering said composition to said subject.

Use of a substituted imidazoline compound disclosed herein for the manufacture of a medicament for the treatment of an inflammatory disease.

Use of a substituted imidazoline compound disclosed herein for the manufacture of a medicament for the treatment of an autoimmune disease.

Use of a substituted imidazoline compound disclosed herein for the manufacture of a medicament for the treatment of rheumatoid arthritis.

Use of a substituted imidazoline compound disclosed herein for the manufacture of a medicament for the treatment of cancer.

As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity. As used herein, the term "stereoisomer" refers to compounds that have their atoms connected in the same order but differ in the arrangement of their atoms in space.

As used herein, the terms "purified enantiomer" and "purified enantiomer preparation" are meant to indicate a preparation (e.g. derived from a racemic mixture) wherein one enantiomer has been enriched over the other, and more preferably, wherein the other enantiomer represents less than 10%, and more preferably less than 5%, and still more preferably, less than 2% of the preparation. The purity of enantiomers can be determined by optical rotation or chiral HPLC.

Enantiomers can also be made synthetically. For example, using the TCH-003 R,R-enantiomer as starting material, the TCH-013 enantiomers TCH-018 (R,R) can be readily synthesized using the same protocol as set forth in Example 4. For example, using the TCH-002 S,S-enantiomer as starting material, the TCH-013 enantiomers TCH-017 (S,S) can be readily synthesized using the same protocol as set forth in Example 4.

The present invention contemplates administering (e.g. orally) racemic mixtures, or synthetically-made enantiomers, as well as purified enantiomers, of imidazoline compounds (including but not limited to ester derivates, the two ethyl esters TCH-017 (S,S) enantiomers and TCH-018 (R,R) enantiomers) to patients with diseases, with symptoms of diseases, or simply at risk for disease (e.g. elderly at risk for arthritis).

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

In describing an optically active compound, the prefixes D and L or R and S are used to denote the absolute configuration of the molecule about its chiral center(s). The R and S convention is based on the actual geometry of each enantiomer, using the Cahn-Ingold-Prelog priority rules to classify the form. Molecules with multiple stereogenic centers will have a corresponding number of letters.

In some embodiments, the invention relates to a method of preventing, treating, or managing an inflammatory disease, preferably rheumatoid arthritis, comprising providing a subject diagnosed with, at risk for, or exhibiting symptoms of said disease and a composition comprising an enantiomer of a substituted imidazoline compound disclosed herein, and administering said composition to said subject.

In some embodiments, the invention relates to a method of preventing, treating, or managing cancer comprising providing a subject diagnosed with, at risk for, or exhibiting symptoms of cancer and a composition comprising an enantiomer of a substituted imidazoline compound disclosed herein, and administering said composition to said subject.

Use of an enantiomer of a substituted imidazoline compound disclosed herein for the manufacture of a medicament for the treatment of an inflammatory disease.

Use of an enantiomer of a substituted imidazoline compound disclosed herein for the manufacture of a medicament for the treatment of an autoimmune disease.

Use of an enantiomer of a substituted imidazoline compound disclosed herein for the manufacture of a medicament for the treatment of rheumatoid arthritis.

In some embodiments, the present invention contemplates synthetic methods for conversion of the zwitterion form of a substituted imidazoline compound (including enantiomers) to a salt form (e.g. an HCl salt) that is biologically active. In one embodiment of the method, the specific imidazoline derivative is a) treated with acid and/or base, b) the pH is titrated, and c) the desired product crystallized.

In some embodiments, the invention relates to a method for treating multiple myeloma, comprising: providing a composition comprising TCH-013, and a subject exhibiting symptoms associated with multiple myeloma; and administering said composition to said subject such that said symptoms are reduced. In further embodiments, said composition further comprises a pharmaceutically acceptable carrier. In still further embodiments, the mode of said administration is selected from the group consisting of optical, oral, parenteral, mucosol, buccal, vaginal, rectal, sublingual, inhalation, insufflation, intravenous, intrathecal, subcutaneous and intramuscular.

In a further embodiment, the present invention contemplates an aniline substituted imidazoline. In a still further embodiment, the present invention contemplates a method comprising: a) providing an ethyl ester substituted imidazoline derivative (FIG. 8); and b) functionalizing said derivative at the $R^3$ position with an aromatic substituent. In one embodiment, the aromatic substituent is chosen so as to create a para-chloro substituted racemic imidazoline (FIG. 8).

In a further embodiment, the present invention contemplates functionalization of a benzyl group of the disclosed imidazoline derivatives (including but not limited to TCH-013) with a lipophilic moiety, such as the lipophilicpara-bromo moiety.

BRIEF DESCRIPTION OF THE FIGURES

FIG. 2 shows data of inhibition for embodiments of the invention.
FIG. 3 illustrates embodiments of the invention.

FIG. 6 shows data of preferred embodiments of the invention. (a)=Log $EC_{50}$ values for inhibition of luciferase production in pNF-κB-luc HeLa cells following TNF-α activation. (b)=Standard error of log $EC_{50}$ values for inhibition of luciferase production in pNF-κB-luc HeLa cells following TNF-α activation. (c)=$EC_{50}$ values calculated from the log $EC_{50}$ values for inhibition of luciferase production in pNF-κB-luc HeLa cells following TNF-α activation. (d)=Log $IC_{50}$ values for inhibition of TNF-α production in human whole blood following IL-1β, stimulation. (e)=Standard error of log $IC_{50}$ values for inhibition of TNF-α production in human whole blood following IL-1β stimulation. (f)=$IC_{50}$ values calculated from the log $IC_{50}$ values for inhibition of TNF-α production in human whole blood following IL-1β stimulation. (g)=Log $IC_{50}$ values for inhibition of IL-6 production in human whole blood following IL-1β stimulation. (h)=Standard error of log $IC_{50}$ values for inhibition of IL-6 production in human whole blood following IL-1β stimulation. (i)=$IC_{50}$ values calculated from the log $IC_{50}$ values for inhibition of IL-6 production in human whole blood following IL-1β stimulation.

FIG. 7 shows data of preferred embodiments of the invention. (a)=Log $EC_{50}$ values for inhibition of luciferase production in pNF-κB-luc HeLa cells following TNF-α activation. (b)=Standard error of log $EC_{50}$ values for inhibition of luciferase production in pNF-κB-luc HeLa cells following TNF-α activation. (c)=$EC_{50}$ values calculated from the log $EC_{50}$ values for inhibition of luciferase production in pNF-κB-luc HeLa cells following TNF-α activation. (g)=Log $IC_{50}$ values for inhibition of IL-6 production in human whole blood following IL-1β stimulation. (h)=Standard error of log $IC_{50}$ values for inhibition of IL-6 production in human whole blood following IL-1β stimulation. (i)=$IC_{50}$ values calculated from the log $IC_{50}$ values for inhibition of IL-6 production in human whole blood following IL-1β stimulation.

FIG. 9 shows data of preferred embodiments of the invention. (a)=Log $EC_{50}$ values for inhibition of luciferase production in pNF-κB-luc HeLa cells following TNF-α activation. (b)=Standard error of log $EC_{50}$ values for inhibition of luciferase production in pNF-κB-luc HeLa cells following TNF-α activation. (c)=$EC_{50}$ values calculated from the log $EC_{50}$ values for inhibition of luciferase production in pNF-κB-luc HeLa cells following TNF-α activation. (g)=Log $IC_{50}$ values for inhibition of IL-6 production in human whole blood following IL-1β stimulation. (h)=Standard error of log $IC_{50}$ values for inhibition of IL-6 production in human whole blood following IL-1β stimulation. (i)=$IC_{50}$ values calculated from the log $IC_{50}$ values for inhibition of IL-6 production in human whole blood following IL-1β stimulation.

Figure 11:
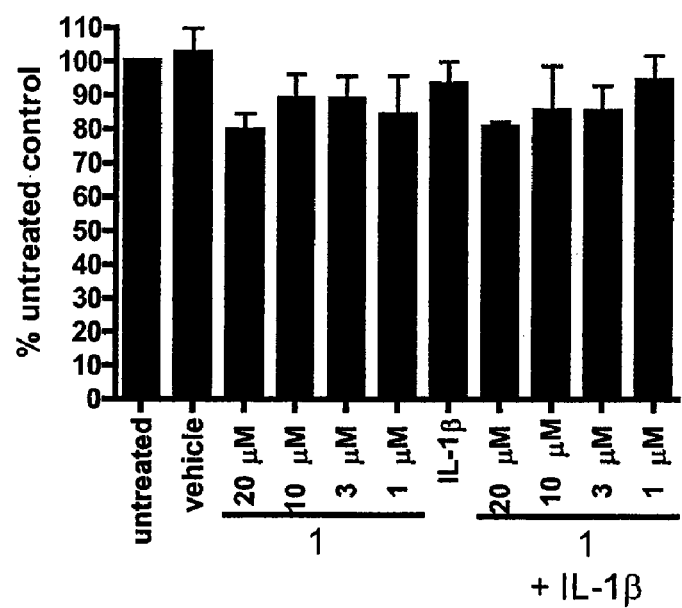

FIG. 11 shows the cytotoxicity of TCH-013. Human blood was exposed to TCH-013 (imidazoline 1) for 24 hours at various concentrations and the lymphocytes were evaluated for survival.

DETAILED DESCRIPTION OF THE INVENTION

The invention relates to biologically active imidazolines that are inhibitors of the NF-κB pathway including salt forms, enantiomers and prodrugs. In preferred embodiments, the zwitter ions, salt forms or prodrugs in the forms of esters of the described imidazoline compounds impart biological activity. It is contemplated that structural modifications of the imidazolines described herein that alter the zwitter ionic character of the molecule for the purpose of enhancing biological activity. These compounds inhibit cytokine product in human blood as evidence of utility in the treatment for diseases including inflammatory diseases, cancer, and others.

Inflammatory diseases include, but are not limited to, chronic obstructive pulmonary disease, or COPD; osteoarthritis (OA); rheumatoid arthritis (RA); inflammatory bowel disease (IBD); Psoriasis; and Artherosclerosis.

Chronic obstructive pulmonary disease (COPD) is a group of progressive lung diseases characterized by airflow obstruction or limitation that is not fully reversible. The restricted airflow is generally progressive and associated with abnormal inflammatory response of the lungs to irritants. The family of diseases includes chronic bronchitis, emphysema and bronchiectasis.

Osteoarthritis (OA) is characterized by mild to debilitating pain, which can involve almost any joint but, in particular, weight bearing joints such as the hip, knee, spine and feet. OA refers to a degeneration of the articular cartilage that makes up the joint surface. This breakdown removes the soft buffer between the bones and can, when severe, result in bone against bone friction, which can cause severe pain and loss of movement. Symptoms include joint pain or aching—at the time of exercise but also when resting if the osteoarthritis is severe, and reduced movement and progressive stiffness of the joint.

Rheumatoid arthritis (RA) is a chronic systemic inflammatory disease of undetermined etiology involving primarily the synovial membranes and articular structures of multiple joints. The disease is often progressive and results in pain, stiffness, and swelling of joints. In late stages deformity and ankylosis develop. The diagnosis is based routinely on the persistence of arthritic symptoms over time. The application of classification systems based on qualifying symptom criteria or on decision-tree methodology also aids in establishing a diagnosis. The primary targets of inflammation are synovial membranes and articular structures. Other organs are affected as well. Inflammation, proliferation, and degeneration typify synovial membrane involvement. Joint deformities and disability result from the erosion and destruction of synovial membranes and articular surfaces. The disease course may be short and limited or progressive and severe.

RA is usually a disease of insidious onset, although it can be abrupt. The diagnosis typically is made when several of the qualifying criteria established by the American Rheumatism Association are met. These qualifying criteria are as follows: morning stiffness lasting longer than 1 hour before improvement; arthritis involving 3 or more joints; arthritis of the hand, particularly involvement of the proximal interphalangeal (PIP) joints, metacarpophalangeal (MCP) joints, or wrist joints; bilateral involvement of joint areas (i.e., both wrists, symmetric PIP and MCP joints); positive serum rheumatoid factor (RF); rheumatoid nodules; radiographic evidence of RA.

No cure for rheumatoid arthritis is presently available. The only small molecule therapy for disease modification in rheumatoid arthritis, methotrexate, is effective in only approximately 20% of RA patients and it's use is limited by toxicity issues at higher exposures. The most effective disease modifying approaches currently in use for RA rely on protein therapeutic agents that interfere with signaling by the potent proinflammatory cytokines, TNF-α (Infliximab, Adalimumab, Etanercept,) and IL-1β (Anakinra), or an anti-CD20 monoclonal antibody (Rituximab) that depletes B-cells. These biologics are expensive therapeutics, require parenteral administration, and have variable responses in patients. Furthermore, the cytokine-targeting protein therapeutics act by preventing activation of cellular receptors, which themselves activate the NF-κB signaling pathway.

Inflammatory Bowel Disease (IBD) is the name of a group of disorders that cause the intestines to become inflamed (red and swollen). IBD can be painful and debilitating and causes chronic inflammation of the digestive tract. The two most common forms of IBD are ulcerative colitis and Crohn's Disease. Both conditions inflame the lining of your digestive tract and both can cause severe bouts of watery diarrhoea and abdominal pain.

Psoriasis is a common immune-mediated chronic skin disease that comes in different forms and differing levels of severity. It is a condition that is generally found on the knees, elbows, scalp, hands, feet or lower back, and generally appears as patches of raised red skin covered by a flaky white build up. It can cause intense itching and burning Artherosclerosis is the term for the process of fatty substances, cholesterol, cellular waste products, calcium and fibrin building up in the inner lining of an artery. The first symptom of a narrowing artery may be pain or cramps at times when the blood flow can't keep up with the body's demand for oxygen. For example, during exercise a person may feel chest pain because of a lack of oxygen to the heart or while walking, a person may feel leg cramps because of a lack of oxygen to the legs.

It is contemplated for the certain embodiments of the invention, the pharmaceutical compositions disclosed have the ability to effectively treat new patient segments based on the novel mechanism-of-action used; provide for oral dosing; and have a reduced toxicity profile.

NF-κB is a ubiquitous transcription factor that regulates more than 150 genes, impacting virtually every aspect of cellular adaptation, including responses to stress, inflammatory stimuli, activation of immune cell function, cellular proliferation and programmed cell death (apoptosis), and oncogenesis. Genes that are regulated by NF-κB include various cytokines (IL-1, IL-2, TNF-α, and IL-6), chemokines (IL-8 and RANTES), cell adhesion molecules (ICAM 1, VCAM-1, and E-selectin), growth factors, cyclin D1, cyclooxyenase (COX-2), matrix metalloproteinase (MMP-9) and others. Given the role that NF-κB plays in the regulation of vcellular processes, it is not surprising that diseases result when NF-κB-dependent transcription becomes dysregulated. Aberrant and prolonged activation of NF-κB has been implicated in a number of pathologies including rheumatoid arthritis, inflammatory bowel disease, and cancer. Consequently, the inhibition of NF-κB activation has been a focus of intense academic and industrial research as a strategy for developing novel therapeutic interventions to address unmet medical needs in major chronic illnesses.

NF-κB is comprised of a group of five proteins, namely c-Rel, Rel A (p65), Rel B, NF-κB1 (p50 and p105), and NF-κB2 (p52). NF-κB activation is held in check by a family of regulatory inhibitors called inhibitory-kappaBs (IκB). In an inactive state, NF-κB resides in the cytoplasm primarily as a heterotrimer consisting of p50, p65, and IκBα subunits. In response to an activation signal, the IκBα subunit is phosphorylated at serine residues 32 and 36, which initiates the ubiquitination of IκB by the SCF-β-TrCP E3 ligase, on lysine residues 21 and 22. Proteosomal digestion of the ubiquitinated NF-κB signalosome then exposes nuclear localization signal sequences on the resulting p50-p65 heterodimer. The p65-subunit of NF-κB is subsequently phosphorylated, leading to nuclear translocation, specific DNA sequence binding and gene transcription.

Activation of NF-κB by TNF-α and IL-1β plays a role in the inflammatory process by inducing the transcription of a host of pro-inflammatory cytokines, chemokines, adhesion molecules, and COX-2, resulting in the modulation of critical cellular functions such as apoptosis and osteoclastogenesis. The role of NF-κB in these processes makes it a compelling target for therapeutic intervention in inflammatory arthritis.

Several groups have reported positive results with inhibitors of NF-κB activation in animal models of arthritis. Two labs have reported that IKK inhibitors IMD-0560 and BMS-345541 are effective in inhibiting collagen-induced arthritis in mice. Furthermore, selective inhibition of NF-κB activation blocks osteoclastogenesis and prevents inflammatory bone destruction in vivo. A cell-permeable peptide inhibitor of the IκB-kinase complex has demonstrated a significant reduction in the severity of collagen-induced arthritis in mice as measured by reduced levels of TNF-α and IL-1β, abrogation of joint swelling and reduced destruction of bone and cartilage. In some embodiments, the inventor relates to inhibition of NF-κB activation using compositions disclosed herein for inhibiting chronic inflammatory diseases, including those like RA that involve bone destruction.

Furthermore, research on NOD2, a gene for an intestinal receptor linked to Crohn's disease, has identified NF-κB-mediated overproduction of IL-1β as a probable cause of the severe intestinal inflammation in this disease. In some embodiments, the invention relates to compositions disclosed herein that contain inhibitors of NF-κB for the prevention and/or treatment of Crohn's disease.

In addition to these inflammatory diseases, a function of NF-κB is the promotion of cell survival through the induction of anti-apoptotic genes, whose products inhibit apoptotic signaling in normal and cancerous cells. Inhibition of the nuclear translocation of NF-κB blocks induction of antiapoptotic gene transcription and sensitizes tumor cells to chemotherapeutic agents. One can control inducible chemoresistance through inhibition of NF-κB using a mutated form of IκBα, the endogenous inhibitor of NF-κB. The overexpression of a mutated IκBα directly regulated the cytotoxicity caused by camptothecin illustrating the clinical relationship of NF-κB inhibitors in combination chemotherapy, potentiating the efficacy of existing chemotherapeutic agents and attenuating NF-κB survival signaling in cancer cells.

Bortezomib (Velcade®, PS-341, Millennium Pharmaceuticals), a 20S proteasome inhibitor that reduced NF-κB mediated gene transcription, was validated in the clinic for treating cancer patients with refractory or relapsed multiple myeloma. Bortezomib is approved in the United States (2003) and Europe (2004) for the treatment of multiple myeloma in patients who have received at least two prior therapies.

In some embodiments, the invention relates to a method for reducing the symptoms associated with multiple myeloma. Multiple myeloma (MM) cells contain constitutively activated levels of NF-κB and are very resistant to classical chemotherapeutic treatment. Pretreatment of MM cells with Bortezomib shows efficacy when used in conjunction with traditional anticancer therapies as disclosed in Ma et al. (2003) Clinical Cancer Research 9, 1136-1144 and Hideshima et al. (2002) Journal of Biological Chemistry 277, 16639-16647, both of which are incorporated herein by reference, although prolonged drug exposure has resulted in cumulative toxicity and chemoresistance as provided for in Chauhan et al. (2004) Blood 104, 2458-2466, incorporated in its entirety by reference. Bortezomib has been approved in the United States and Europe for the treatment of MM. While not limiting the scope of the present invention, it is believed that the bone marrow microenvironment in MM patients promotes MM cell survival and tumor expansion primarily via the activation of several complex signaling networks, including the NF-κB, IL-6R/STAT3, Ras/MAPK and PI3K/Akt signaling pathways as provided for in Bommert et al. (2006) European Journal of Cancer 42, 1574-1580 and Tu et al. (2000) Cancer Research 60, 6763-6770, both of which are incorporated herein by reference. The aberrant and prolonged activation of NF-κB has been directly implicated in the pathogenesis of MM as disclosed in Chauhan et al. (1996) Blood 87, 1104-1112 and Hideshima et al. (2001) Oncogene 20, 4519-4527, both of which are incorporated herein by reference. Bone marrow aspirates of MM patients indicate that NF-κB is constitutively expressed, which is considered to be a major factor in chemoresistance due to an increased expression of anti-apoptotic cell signaling as provided for in Bharti et al. (2003) Blood 101, 1053-1062, incorporated in its entirety by reference. The interaction of MM cells with its bone marrow microenvironment is responsible for constitutive activation of NF-κB, making MM cells very resistant to classical chemotherapeutic treatment as disclosed in Bharti et al. While not limiting the present invention to any particular theory, it is postulated that MM cells attach to bone marrow stromal cells (BMSCs), resulting in the activation of NF-κB and subsequent upregulation of IL-6 and receptor activator of NF-□B ligand (RANKL) in both BMSCs and osteoclasts (FIG. 1) as provided for in Hideshima et al. (2007) Nature Reviews Cancer 7, 585-598 and Hideshima et al. (2004) Blood 104, 607-618, both of which are hereby incorporated by reference. Similar to BMSCs, osteoclasts also strongly enhance contact mediated growth and survival of MM cells, resulting in a vicious cycle of bone destruction and tumor growth as disclosed in Zangari et al. (2006) Clinical Lymphoma and Myeloma 7, 109-114, incorporated herein by reference. It is believed that NF-κB mediated-IL-6 signaling protects MM cells from apoptosis by induction of survival pathways, anti-apoptotic pathways and induction of proliferation as provided for in Chiang et al. (2004) Cancer Biology and Therapy 3, 1018-1020 and Chatterjee et al. (2002) Blood 100, 3311-3318, both of which are hereby incorporated by reference. Additionally, IL-6 is required for terminal differentiation of B cells and is critical in the pathogenesis and growth of MM as disclosed in Klein et al. (1995) Blood 85, 863-872, incorporated in its entirety by reference.

Consequently, inhibition of the IL-6-controlled IL6R/STAT3 pathway induces apoptosis in MM cells as provided for Chatterjee et al. Blood 104, 3712-3721, incorporated by reference. Previous studies found that IL-6 knockout mice fail to develop plasma cell tumors as disclosed in Hilbert et al. (1995) Journal of Experimental Medicine 182, 243-248, incorporated in its entirety by reference. Thus, IL-6 signaling is considered the central growth factor in the pathogenesis of multiple myeloma and as a result, suppression of the cytokine IL-6 is a promising approach to treating MM as provided for in Chiang et al. (2004) *Cancer Biology and Therapy* 3, 1018-1020; Bommert et al. (2006) *European Journal of Cancer* 42, 1574-1580 and Rose-John et al. (2007) *Expert Opinions on Therapeutic Targets* 11, 613-624, all of which are hereby incorporated by reference. It was previously found that the combination of IL-6 antibodies with current MM therapies such as Bortezomib were found to have very promising pre-clinical results as provided for in Park et al. (2008) *Anticancer Drugs* 19, 777-782 and Voorhees et al. (2007) *Clinical Cancer Research* 13, 6469-6478, both of which are incorporated herein by reference. Unfortunately, clinical trials with specific IL-6 blocking antibodies demonstrated that inhibition of IL-6 alone resulted in no significant clinical response, due to alternative cytokine signaling as disclosed in Chatterjee et al. (2006) *European Journal of Cancer* 42, 1640-1652 and Trikha et al. Clinical Cancer Research 9, 4653-4665, both of which are incorporated by reference. Reduction of IL-6 levels via the inhibition of transcription factors such as NF-κB, which regulates multiple cytokines in addition to IL-6 (such as TNF-α, IL-2, IL-8) may provide a significant advantage over a specific antibody therapy.

In some embodiments, the invention relates to a method of treating patients both as a single agent and in combination with other chemotherapeutic agents, for cancer and hematological malignancies such as mantle cell lymphoma and marginal zone lymphoma. It is also contempated that these compositions can be used for treating or preventing graft-versus-host disease (GVHD) in which transplanted effector cells attack various cells and tissues of the recipient (host).

In some embodiments, the invention relates to esters and amides (including pro-drugs or active analogues) of the described imidazoline drugs possessing biological activity. Also claimed herein are structural modifications of the imidazolines described containing ester and amide prodrugs or active analogues. Examples include the esters and amides listed in FIGS. 1 through 5. These compounds exhibit micromolar inhibition in a NF-κB mediated Luciferase activity in a HeLa reporter assay as well as NF-κB mediated inhibition of TNF-a production in human blood after IL-1beta stimulation.

The term "salts", as used herein, refers to any anionic and cationic complex, including zwitterions and those anions and cations that complex with compounds disclosed herein including acid addition salts formed with organic acids (e.g., acetic acid, malic acid, fumaric acid, lactic acid, tartaric acid, citric acid, gluconic, salicylic acid, methane sulfonic acid, and benzene sulfonic acid), inorganic acids (e.g. hydrochloric acid, hydrobromic acid, sulfuric acid, phosphoric acid, nitric acid, and the like), and other pharmaceutically acceptable salts as provided in Stahl and Wermuth "Pharmaceutical Salts Properties, Selection, and Use", 1$^{st}$ Ed, Wiley-VCH, 374 (2002).

In particular embodiments of the invention, a preferred salt is a substituted or unsubstituted imidazoline having the following formula:

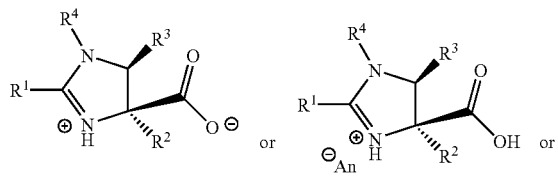

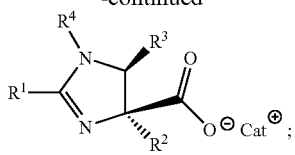

wherein $R^1$, $R^2$, $R^3$, and $R^4$ are the same or differently and independently at each occurrence hydrogen, alkyl, substituted alkyl, aryl, or substituted aryl, and $^-$An is an anion such as the chlorine anion, and $Cat^+$ is a cation such as metal cations or quaternary ammonium cations including nitrogen substituted heteroaryls preferably nitrogen alkylated heteroaryls such as N-substituted pyridines preferably N-alkylated pyridines.

It has been identified that compounds disclosed of varied salt forms, such as the zwitter ionic from and the acid salt form (for example the HCl salt form), vary significantly in there ability to inhibit the NF-κB pathway and invoke biological responses. For example, the zwitter ionic form and HCl salt form of TCH-003 display significantly different potencies in their ability to inhibit TNF-alpha production in the plasma from human whole blood challenged with IL1-beta (See FIG. 1). The zwitter ionic form of THC-003 was inactive in this disease relevant assay of NF-κB activity, where as, the HCl salt form TCH-003-HCl is potent at blocking TNF-alpha production in this assay.

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. When substituted, one or more of the above groups are "substituents." In preferred embodiments, the substituent(s) are one or more halogen(s) such as chloride. In the case of an oxo substituent ("=O"), two hydrogen atoms are replaced. Substituents within the context of this invention also include, deuterium, tritium, borono, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as a saccharide, $-NR_aR_b$, $-NR_aC(=O)R_b$, $-NR_aC(=O)NR_aNR_b$, $-NR_aC(=O)OR_b$ $-NR_aSO_2R_b$, $-C(=O)R_a$, $C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. In addition, the above substituents may be further substituted with one or more of the above substituents, such that the substituent is substituted with halogen, alkyl, substituted aryl, substituted arylalkyl, substituted heterocycle or substituted heterocyclealkyl. $R_a$ and $R_b$ in this context may be the same or different and independently hydrogen, halogen, alkyl, haloalkyl, substituted alkyl, aryl, substituted aryl, arylalkyl, substituted arylalkyl, heterocycle, substituted heterocycle, heterocyclealkyl or substituted heterocyclealkyl. In the context of certain embodiments, a compound may be described as "unsubstituted" meaning that the compound does not contain extra substituents attached to the compound. An unsubstituted compound refers to the chemical makeup of the compound without extra substituents, e.g., the compound does not contain protecting group(s). For example, unsubstituted proline is the proline amino acid even though the amino group of proline may be considered disubstituted with alkyl groups.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkyloxy" means an alkyl moiety attached through an oxygen bridge (i.e., —O-alkyl) such as methoxy, ethoxy, and the like.

"Aryl" means an aromatic carbocyclic moiety such as phenyl or naphthyl.

"Aryloxy" means an aryl moiety attached through an oxygen bridge (i.e., —O-aryl).

"Arylalkyloxy" means an aryl moiety attached through an alkyloxy bridge (e.g., —O—CH$_2$-Phenyl).

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$-morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Isomers" means any of two or more substances that are composed of the same elements in the same proportions but differ in the three dimensional arrangement of atoms including enantiomeric (i.e., mirror images) and diastereomeric isomers.

"Subject" means any animal, preferably a human patient, livestock, or domestic pet.

As used herein, the terms "treat" and "treating" are not limited to the case where the subject (e.g. patient) is cured and the disease is eradicated. Rather, the present invention also contemplates treatment that merely reduces symptoms, and/or delays disease progression.

As used herein, the terms "prevent" and "preventing" include the prevention of the recurrence, spread or onset. It is not intended that the present invention be limited to complete prevention. In some embodiments, the onset is delayed, or the severity of the disease is reduced.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

"Cancer" means any of various cellular diseases with malignant neoplasms characterized by the proliferation of anaplastic cells. It is not intended that the diseased cells must actually invade surrounding tissue and metastasize to new body sites. Cancer can involve any tissue of the body and have many different forms in each body area. Most cancers are named for the type of cell or organ in which they start.

Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, her2 for breast cancer, or others. For example, reduction of cancer may be identified in vitro using the following conditions for evaluation of apoptosis: i) Jurkat human T-cell leukemia cells are passed into flasks (250 mL, 75 cm$^2$) with 20 mL of supporting media; ii) after incubation at 37° C. with 5% CO$_2$, sample compound (or absent control) is added to a flask to make final concentration at 1 mM, and cells are incubated for another day; iii) cells are treated with 10 µM camptothecin and incubated with SYTOX Green reagent and annexin V allophycocyanin (APC) conjugate (invitrogen) and iv) Flow cytometry at 488 nm and 633 nm excitation. In cells undergoing apoptosis, phosphatidylserine (PS) is transferred from the cytoplasmic surface of the cell membrane to the outer leaflet. Annexin V has a high affinity for PS and dye conjugates provide indication of apoptosis by phosphatidylserine exposure and membrane integrity.

Exemplary cancers are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated. Alternatively, cells can be obtained from a subject, treated ex vivo to remove certain undesirable cells, e.g., cancer cells, and administered back to the same or a different subject.

Chemotherapeutic agents that may be co-administered with modulating compounds described herein as having anti-cancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom). In one embodiment, the present invention contemplates administering enantiomers of substituted imidazoline compounds in both a prophylactic treatment (e.g. to patients at risk for disease, such as elderly patients who, because of their advancing age, are at risk for arthritis, cancer, and the like) and therapeutic treatment (e.g. to patients with symptoms of disease or to patients diagnosed with disease).

An "adverse drug reaction" refers to a response to a drug that is noxious and unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity, liver toxicity). Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and *Clostridium difficile* colitis). Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine). Such adverse drug reaction can be determined by subject observation, assay or animal model well known in the art.

A "composition" refers to solid form(s) or mixtures comprising the active compounds (substituted imidazolines) it intended to include nutritional/dietary supplements and bulk-drug compositions useful in the manufacture of pharmaceutical compositions (e.g., impure or non-sterile compositions) and pharmaceutical compositions (i.e., compositions that are suitable for administration to a subject) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the active compound and another therapeutic or prophylactic agent, and a pharmaceutically acceptable carrier. These compositions may contain between 0.1-99% of the active ingredient In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compound for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles that allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

In other embodiments of the invention, radiation therapy agents such as radioactive isotopes can be given orally as liquids in capsules or as a drink. Radioactive isotopes can also be formulated for intravenous injection. The skilled oncologist can determine the preferred formulation and route of administration.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference (56$^{th}$ ed. 2002, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

In another embodiment, the active compound can be delivered in a vesicle, in particular a liposome.

In yet another embodiment, the active compound can be delivered in a controlled release system. In one embodiment, a pump can be used. In another embodiment, polymeric materials can be used.

The amount of the active compound that is effective in the treatment or prevention of heart conditions can be determined by standard research techniques. For example, the dosage of the active compound which will be effective in the treatment or prevention of heart conditions can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors that will be known to one skilled in the art. Such factors include the disease to be treated or prevented, the symptoms involved, the subject's body mass, the subject's immune status and other factors known by the skilled artisan.

The precise dose to be employed in the formulation will also depend on the route of administration, and the seriousness of the disease-related wasting, and should be decided according to the judgment of the practitioner and each subject's circumstances. Effective doses can be extrapolated from dose-response curves derived from in vitro or animal model test systems.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

A popular cancer drug is taxol. Typical dosage ranges of taxol include less than 10 mg to 100 mg or more. Particular doses of taxol include about 5 mg, 10 mg, 20 mg, 40 mg, 50 mg, 60 mg, 80 mg, 100 mg, 150 mg and 200 mg. Typically, these are daily dosages. Generally, higher dosages are less preferred because of potential gastric disturbances. Therapeutic dosages may range between 40 to 80 mg per day when tolerable by a subject.

The invention provides for any method of administrating lower doses of known agents (e.g., taxol) than previously thought to be useful for the prevention or treatment of cancer.

The invention provides a pharmaceutical pack or kit comprising one or more containers containing an active compound and optionally one or more other prophylactic or therapeutic agents useful for the prevention or treatment of cancer. The invention also provides a pharmaceutical pack or kit comprising one or more containers containing one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for the composition's use.

EXAMPLES

Example 1

Preparation of Salt Forms

The ionic form of the described imidazoline compounds can be controlled by treating a specific imidazoline derivative with acid, base, titrating the pH, crystallizing from various media, and modifying the chemical structure to alter the isoelectic point. Imidazoline disclosed herein were prepared using procedures and starting materials as provided or appropriately modified as disclosed in U.S. Pat. No. 6,878,735, Organic Letters (2002), 4, 459-461, and Synthesis (2003), 9, 1433-1440.

Example 2

Conversion of the Zwitterion to HCl Salt

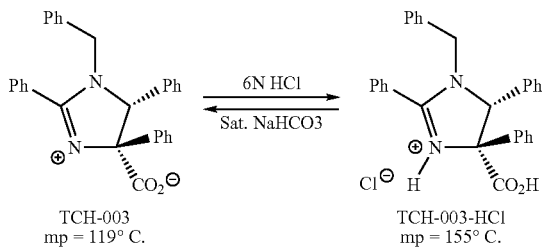

TCH-003 (Zwitterion, 200 mg, 0.46 mmol) was dissolved in DCM (20 mL) and placed in a separatory funnel. Then washed with 6N HCl (2×2 mL) and pH of the aqueous layer was checked and at 1-2. The organic fraction was separated, dried over $MgSO_4$, filtered and concentrated in vacuo to yield a white crystalline solid (quantitative yield). m.p. 152-155° C.

Example 3

Activity of Zwitter Ionic and HCl Salt Forms of TCH-003

Figure 1:
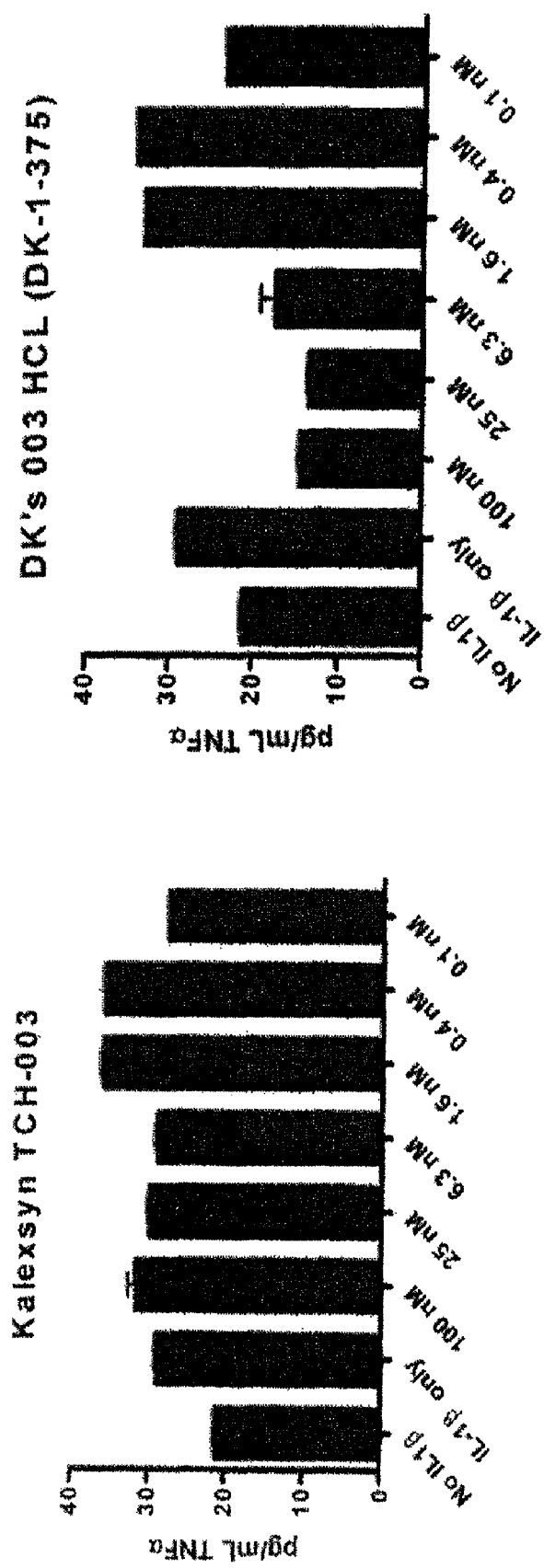
FIG. 1 shows data comparing inhibition based on salt forms.
Figure 4:
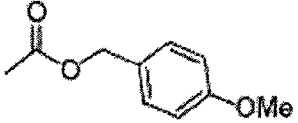
FIG. 4 illustrates embodiments of the invention.
Figure 4:
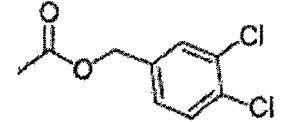
Figure 4:
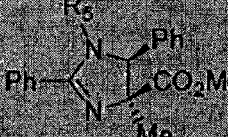
Figure 4:
Figure 5:
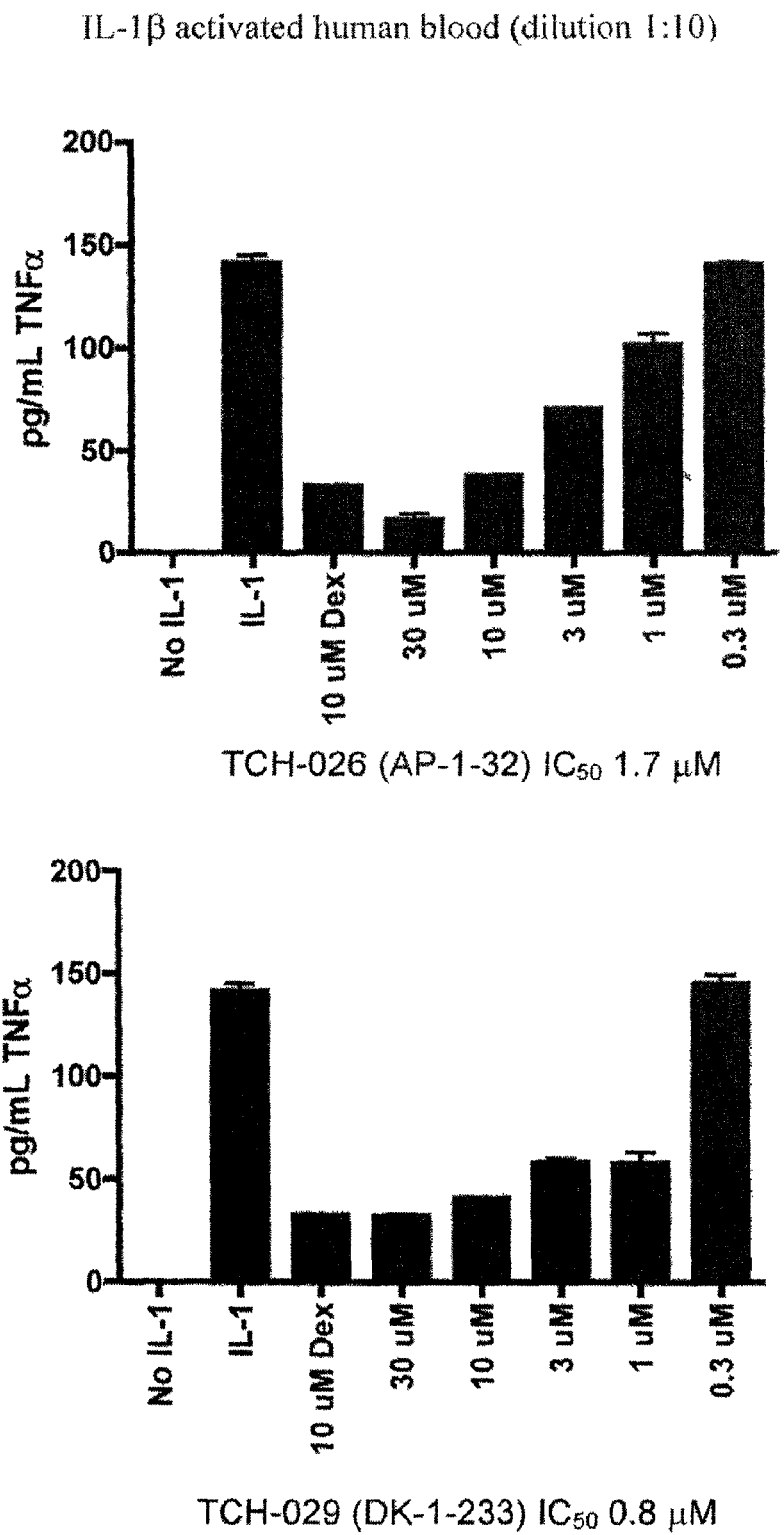
FIG. 5 shows data of preferred embodiments of the invention.

FIG. 1 shows that the zwitter ionic form of TCH-003 does not inhibit TNF-alpha inhibition at a concentration range of 0.1-100 nM relative to IL-1-beta control. Conversely, the HCl form, TCH-003-HCl, significantly inhibits TNF-alpha production stimulated by IL-1-beta in whole blood at several concentrations. The experimental protocol was for this assay was conducted according to the procedure of human blood (Valley Biomedical whole blood) was challenged with IL-1β, in order to activate the NF-κB signaling pathway. TNF-α expression (an NF-κB gene product) was monitored over time (0→180 minutes) using an ELISA assay, in the presence and absence of the zwitterionic TCH-003 and the HCl salt (DK-1-375) Samples were incubated for 30 min at 37° C., after which human IL-1β (200 units or 50 ng/mL) or saline vehicle was added and the incubations continued at 37° C. Incubations were terminated at various times up to 3 hours following IL-1β addition by centrifugation to isolate blood plasma. Plasma TNF-α concentration was evaluated using a commercial ELISA kit. As indicated in the figure below, the HCl salt of TCH-003 was capable of completely blocking the TNF-α expression after IL-1β stimulation.

Example 4

Synthesis of Ester TCH-013

While enantiomers of TCH-013 can be prepared (e.g. by using TCH-003, which is the RR enantiomer of TCH-001), in this example, TCH-013 is racemic and is prepared from the racemic compound TCH-001. Into a flame-dried flask under nitrogen was placed TCH-001 and DCM. After cooling the reaction mixture to 0° C., oxalyl chloride was added over 5 min. followed by DMF (2 drops). The reaction mixture was allowed to stir at 0° C. for 2 h after which the solvent was removed on the rotoevaporator. The residue was placed on a vacuum line for 1 hr. The flask was then placed under nitrogen and cooled to 0° C. and was added EtOH. After stirring for an addition 2.5 h the EtOH was removed on the rotoevaporator and DCM was added. The organic solution was washed with sat. aq. $NaHCO_3$ and $H_2O$, dried over $MgSO_4$, filtered and concentrated in vacuo. The product was purified using flash column chromatography with 1:1 hexanes:EtOAc as eluent to give a white foamy material (73%).

Alternative one may make esters using the following protocol. To a stirred solution of TCH-001 (0.12 mmol, 1.0 eq) in DCM was added EDCI (0.17 mmol, 1.5 eq). After 5 min was added 4-DMAP (0.12 mmol, 1.0 eq). After stirring for an addition 10 min. benzylalcohol (0.23 eq, 2.0 eq) was added. The reaction mixture was stirred at room temperature overnight. The reaction mixture was washed with 10% HCl (1×5 mL), sat. aq. $NaHCO_3$ (1×5 mL), $H_2O$ (1×5 mL) and brine (1×5 mL). The product was extracted using DCM, dried over $MgSO_4$, filtered and concentrated in vacuo. The product was purified using flash column chromatography with 9:1 DCM: EtOAc as eluent.

Similarly the compounds disclosed in FIGS. 1-5 where prepared using procedures above or as appropriately modified using starting materials disclosed in U.S. Pat. No. 6,878,735, hereby incorporated by reference.

Example 5

Synthesis of Amide TCH-015

To a stirred solution of TCH-001 (0.21 mmol, 1.0 eq), HOBt (0.23 mmol, 1.1 eq), EDCI (0.23 mmol, 1.1 eq) in anhydrous THF (2 mL) was added DIPEA (0.23 mmol, 1.1 eq). The reaction mixture was stirred at ambient temperature for 10 min. Then $(NH_4)_2CO_3$ was added in one portion and the resulting suspension was stirred at ambient temperature overnight. The reaction mixture was concentrated to minimal residue. The residue was treated with 1:1 sat. aq. $NaHCO_3$: $H_2O$ (2 mL) and stirring was continued for 2 h. The mixture was placed into a separatory funnel and the product was extracted using EtOAc, dried over $MgSO_4$ and concentrated in vacuo. The product was purified using flash column chromatography with 30% hexanes: EtOAc as eluent (71%).

Example 6

Preparation of RM-2-071 azido and Reduction to the amine

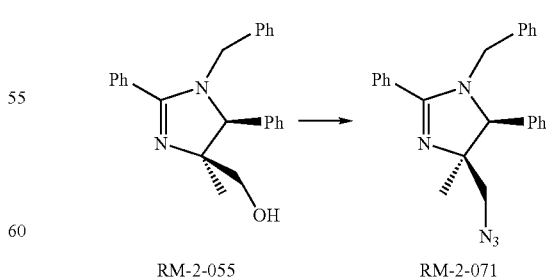

(4R,5S)-4-(azidomethyl)-1-benzyl-4,5-dihydro-4-methyl-2, 5-diphenyl-1H-imidazole (RM-2-071). To a stirring solution of RM-2-055 (0.2539 g, 0.71 mmol) in pyridine (4.0 mL) cooled to 0° C. in a flame dried flask was added methanesulfonyl chloride (0.28 mL, 3.60 mmol), and the reaction stirred until complete by TLC. The reaction was diluted with CH$_2$Cl$_2$ (5 mL), and the organic layer was washed successively with water and brine. The crude product was dried (Na$_2$SO$_4$) and concentrated, and was then diluted in dry DMF (5 mL). NaN$_3$ (0.1923 g, 2.96 mmol) was added and the reaction stirred at 80° C. under nitrogen atmosphere for 30 hours. The resulting suspension was filtered and the collected solid was washed successively with hexanes and CH$_2$Cl$_2$. The combined filtrate and organic washes were washed with brine, dried (Na$_2$SO$_4$), and concentrated, and 0.2097 g of RM-2-071 (77% yield) was collected as a white solid (m.p.=82-84° C.) $^1$H NMR (300 MHz) (CDCl$_3$) δ TMS: 1.31 (3 H, s), 3.00 (2 H, dd, J=12.1 Hz, J=36.5 Hz), 3.84 (1 H, d, J=15.7 Hz), 4.20 (1 H, s), 4.69 (1 H, d, 15.4 Hz), 6.90 (2 H, m), 7.20-7.46 (11 H, m), 7.70 (2 H, m). $^{13}$C NMR (75 MHz) (CDCl$_3$) δ: 27.0 (s), 48.8 (s), 57.6 (s), 71.2 (s), 71.9 (s), 127.5 (s), 127.8 (s), 128.0 (s), 128.4 (s), 128.5 (s), 128.6 (s), 128.6 (s), 130.1 (s), 131.0 (s), 136.2 (s), 136.5 (s), 165.1 (s). IR (KBr pellet): 2102, 1617, 1599, 1575, 1496, 1452, 1407, 1305.

Example 7

Preparation of TCH-024

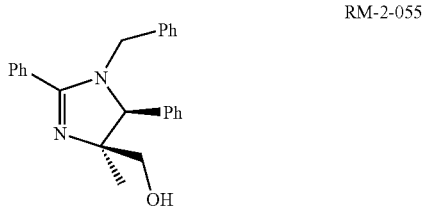

RM-2-055

((4S,5S)-1-benzyl-4,5-dihydro-4-methyl-2,5-diphenyl-1H-imidazol-4-yl)methanol (RM-2-55, also named TCH-024). To a suspension of LiAlH$_4$ (0.0542 g, 1.43 mmol) in anhydrous THF (110 mL) at 0° C. was added a solution of (4S, 5S)-methyl 1-benzyl-4,5-dihydro-4-methyl-2,5-diphenyl-1H-imidazole-4-carboxylate (0.3450 g, 0.90 mmol) in THF (20 mL). The mixture stirred at 0° C. under N$_2$ until complete by TLC. Saturated NH$_4$Cl solution (20 mL) was added to and the reaction stirred for 10 minutes as it warmed to room temperature. The organic layer was extracted with EtOAc (30 mL) and the aqueous layer was washed with EtOAc (3×20 mL). The combined organic fractions were washed with brine (3×30 mL), dried (Na$_2$SO$_4$), and evaporated to dryness under vacuum to give 0.1837 g of RM-2-055 (57% yield) as a white solid (m.p.=158° C.) after column chromatography on silica gel (15% MeOH/85% EtOAc).

$^1$H NMR (300 MHz) (CDCl$_3$) δ TMS: 1.30 (3 H, s), 3.01 (2 H, dd, J=11.4 Hz, J=28.43 Hz), 3.38 (1 H, br. s), 3.81 (1 H, d, J=15.4 Hz), 4.19 (1 H, s), 4.67 (1 H, d, 15.4 Hz), 7.19 (2 H, m), 7.10-7.50 (11 H, m), 7.65 (2 H, m). $^{13}$C NMR (75 MHz) (CDCl$_3$) δ: 26.1 (s), 48.8 (s), 67.2 (s), 71.9 (s), 127.5 (s), 127.8 (s), 128.4 (s), 128.5 (s), 128.6 (s), 128.7 (s), 130.1 (s), 130.9 (s), 136.3 (s), 165.0 (s). IR (NaCl, neat): 3174, 1593. MS (GCMS), calcd for C$_{24}$H$_{24}$N$_2$O (M$^+$): 356.19. Found: 356.3. Anal. Calcd. For C$_{24}$H$_{24}$N$_2$O: C, 80.87; H, 6.79; N, 7.86. Found: C, 78.56; H, 6.64; N, 7.58.

Example 8

Synthesis and Testing of Enantiomers

Of the ester derivates, the two ethyl esters TCH-017 (S,S) enantiomers and TCH-018 (R,R) enantiomers were prepared using the identical procedures as described in Example 4 (see above). Both enantiomers were thereafter tested for their ability to inhibit NF-κB mediated gene transcription using a luciferase reporter assay, using a stable transfected HeLa cells. As shown in FIG. 6, TNF-alpha induced NF-κB-mediated luciferase activity was reduced in the presence of TCH-017 and TCH-018, with EC50 values of 2.3 and 0.9 micromolar. This data indicates that, of the two compounds, the R,R enantiomers (TCH-018) is preferred.

Example 9

Comparison with Whole Blood Assay

In this example, a series of imidazolines were tested for their activity to inhibit NF-κB mediated inhibition of luciferase activity (using the assay described above) as well as their ability to inhibit NF-κB mediated production of TNF-alpha in human blood. The whole blood assay is as follows: Human whole blood was challenged with IL-1β in order to activate the NF-κB signaling pathway. TNF-α expression (an NF-κB gene product) was measured after 24 hours using an ELISA assay, in the presence and absence of the imidazolines (experiments performed in duplicate). Samples were incubated for 30 min at 37° C., after which human IL-1β (200 units or 50 ng/mL) or saline vehicle was added and the incubations continued at 37° C. Incubations were terminated after 24 hours following IL-1β addition by centrifugation to isolate blood plasma. Plasma TNF-α concentration was evaluated using a commercial ELISA kit. The data indicates the imidazolines, block the NF-κB mediated TNF-α production in human blood at low micromolar concentrations.

As seen in the table below, the inhibition of NF-κB mediated luciferase activity in HeLa cells corresponded with the inhibition of NF-κB mediated TNF-alpha production in human blood.

Example 10

Inhibitors of Multiple Myeloma (MM)

Compounds 10-14 were evaluated for their ability to inhibit NF-κB-mediated luciferase production in cell culture as well as NF-κB-mediated IL-6 production in stimulated human blood (FIG. 7). Human whole blood was incubated with the imidazolines 10-14, for 2 hours and was subsequently activated with IL-1β, which induced an NF-κB mediated cytokine response. IL-1β induced cytokine production was measured 22 hours after stimulation using IL-6 production using a human IL-6 ELISA (R&D Systems). Similar to the HeLa NF-κB-luc assays, compounds 10 and 14 were found to be the most potent with IC$_{50}$ values of 3.0 and 4.0 μM, respectively, for inhibition of IL-1β stimulated IL-6 production. Since compound 10 proved to be slightly more active than compound 5, phenyl glycine was chosen as the preferred R$^1$ position. It should be noted that this small screen was preformed on the methyl ester substituted imidazolines instead of what was later found out to be the more potent ethyl ester derivatives (compare activities of 1 versus 10). Even though this short screen will be repeated with the more potent ethyl ester derivatives, the relative activities clearly shown that the R$_2$ domain can be readily substituted with a range of large substituents to retain activity.

Figure 8:
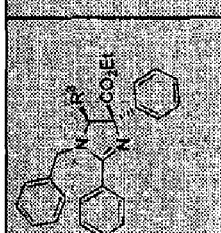
FIG. 8 shows data of preferred embodiments of the invention. (a)=Log $EC_{50}$ values for inhibition of luciferase production in pNF-κB-luc HeLa cells following TNF-α activation. (b)=Standard error of log $EC_{50}$ values for inhibition of luciferase production in pNF-κB-luc HeLa cells following TNF-α activation. (c)=$EC_{50}$ values calculated from the log $EC_{50}$ values for inhibition of luciferase production in pNF-κB-luc HeLa cells following TNF-α activation. (g)=Log $IC_{50}$ values for inhibition of IL-6 production in human whole blood following IL-1β stimulation. (h)=Standard error of log $IC_{50}$ values for inhibition of IL-6 production in human whole blood following IL-1β stimulation. (i)=$IC_{50}$ values calculated from the log $IC_{50}$ values for inhibition of IL-6 production in human whole blood following IL-1β stimulation.

Functionalization of the R$^3$ position of the ethyl ester substituted imidazoline derivative by a range of aromatic substituents also appeared to have a significant affect on the overall activity of the compound (FIG. 8). Minor structural changes had significant affects on overall potency. The 4-pyridino-substituted imidazoline (15) was devoid of activity in our HeLa NF-κB-luc assay and also showed very weak activity (FIG. 8, 12.4 μM) in our whole blood studies, whereas the para-chloro substituted racemic imidazoline 20 is currently the most potent analogue in this series (FIG. 8, $IC_{50}$ 0.3 μM). As seen previously, the two assays corresponded well in terms of their relative potencies. The only possible exception of the consistent correlation between the two assays was the aniline substituted imidazoline, compound 17, which showed moderate to weak activity in the HeLa NF-κB-luc assay and showed excellent activity (FIG. 8, 0.5 μM) in our whole blood assay.

The structural requirement of the $R^4$ domain (FIG. 9) was the synthetically readily accomplished using our 1,3-dicycloaddition reaction. Deletion of this domain, as illustrated by compound 23, rendered the scaffold inactive in both assays. Acylation, benzoylation or tosylation of the imidazoline also decreased its overall activity as illustrated by compounds 24-26. Functionalization of the benzyl group by the lipophilic para-bromo moiety (29) significantly increased its activity compared to the other substitutions in this position as indicated by the compound 27-31. This limited SAR study has already identified 6 racemic compounds with $IC_{50}$ values of less than 1.0 μM for inhibition of NF-κB mediated IL-6 production in human whole blood.

Figure 10:
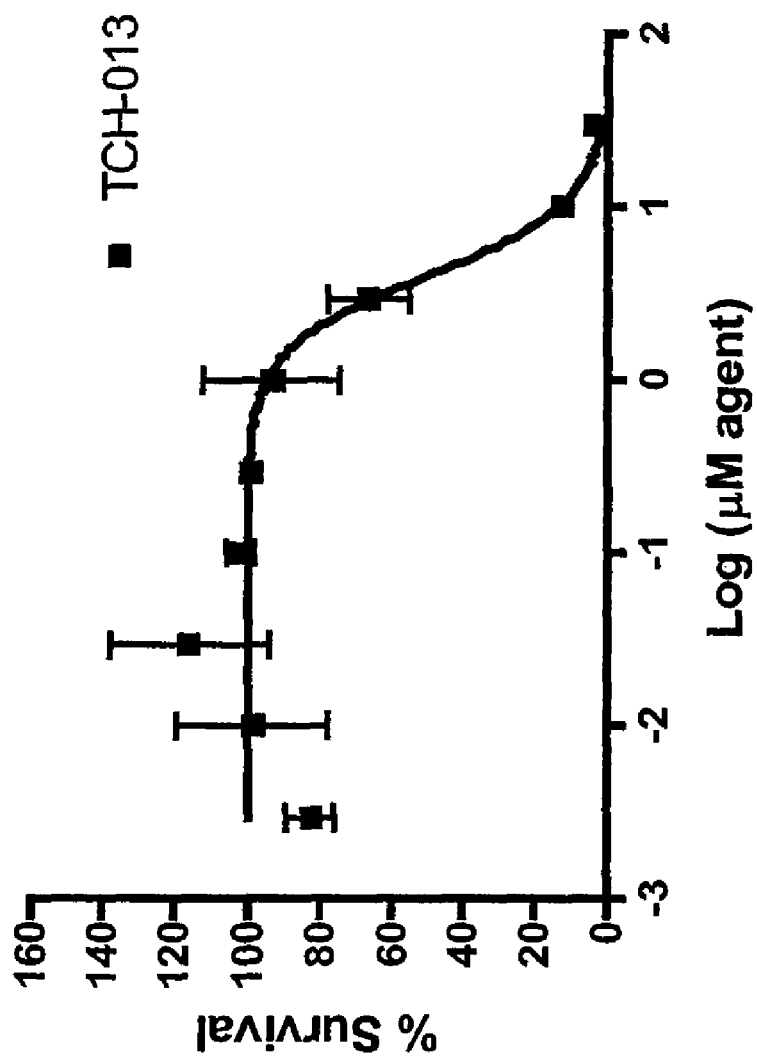
FIG. 10 shows the induction of cell death in MM cells by TCH-013. RPMI-8226 cells were treated with various concentrations of TCH-013 in duplicate and incubated for 24 hours. Percent survival was extrapolated based on mitochondrial activity as determined by MTS assay.

Given the critical role NF-κB-mediated IL-6 production plays in the growth and parthenogenesis of multiple myeloma, we investigated the use of TCH-013 in somewhat more detail in a MM cell line (RPMI-8226). Multiple myeloma is a key target disease for NF-κB as well as IL-6 inhibitors, since nearly all multiple myeloma cells (including RPMI-8226 cells) contains constitutively active NF-κB as provided for in Chauhan et al. (1996) *Blood* 87, 1104-1112; Hideshima et al. (2001) *Oncogene* 20, 4519-4527; Bharti et al. (2003) *Blood* 101, 1053-1062 and Chiang et al. (2004 *Cancer Biology and Therapy* 3, 1018-1020, all of which are hereby incorporated by reference. TCH-013 was found to be effective as a single agent in MM cells. The $CC_{50}$ in the RPMI-8226 MM cell lines was 4.0 μM (FIG. 10), comparable to doxorubicin ($CC_{50}$ 1.2 μM) and better than melphalan ($CC_{50}$ 30.6 μM) in this particular cell line. Importantly, unlike other MM drugs, no significant cytotoxicity towards white blood cells was observed at effective concentrations (<20 μM) (FIG. 11).

What is claimed is:

1. A compound having the following formula:

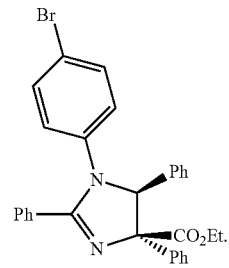

* * * * *